United States Patent [19]

Oberholtzer

[11] Patent Number: 5,545,154
[45] Date of Patent: Aug. 13, 1996

[54] OSTOMY DEVICE

[75] Inventor: Gary E. Oberholtzer, Feasterville, Pa.

[73] Assignee: E. R. Squibb & Sons, Inc., Princeton, N.J.

[21] Appl. No.: 365,714

[22] Filed: Dec. 28, 1994

[51] Int. Cl.$^6$ ..................................................... A61F 5/44
[52] U.S. Cl. ........................................... 604/336; 604/344
[58] Field of Search ........................... 604/332, 336–344

[56] References Cited

U.S. PATENT DOCUMENTS

| | | | |
|---|---|---|---|
| 4,775,374 | 10/1988 | Cilento et al. | 604/338 |
| 5,004,464 | 4/1991 | Leise, Jr. | 604/338 |
| 5,013,307 | 5/1991 | Broida | 604/332 |
| 5,074,852 | 12/1991 | Castellana et al. | 604/336 |

FOREIGN PATENT DOCUMENTS 6109390 11/1993 Australia ................... 604/332

*Primary Examiner*—Mary Beth Jones
*Assistant Examiner*—Dennis Ruhl
*Attorney, Agent, or Firm*—Stuart E. Krieger

[57] ABSTRACT

The hydrocolloid disk includes a polyethylene/PVDC film backing. The disk adheres to the acrylic adhesive layer of the collar over a large portion of the surface area of the disk. The collar is formed of a EVA/polyethylene perforated film on a polyethylene non-woven. In the one piece embodiment, the collar is secured directly to the pouch. In the two piece embodiment, the collar is secured directly to the coupling ring. Increased strength, better odor protection and improved breathability are achieved.

25 Claims, 7 Drawing Sheets

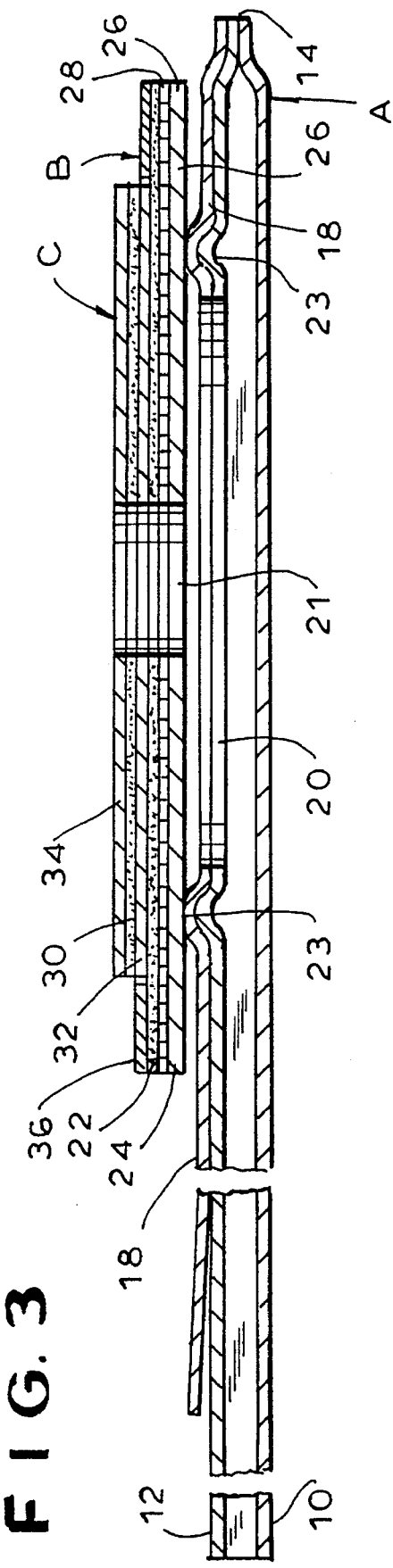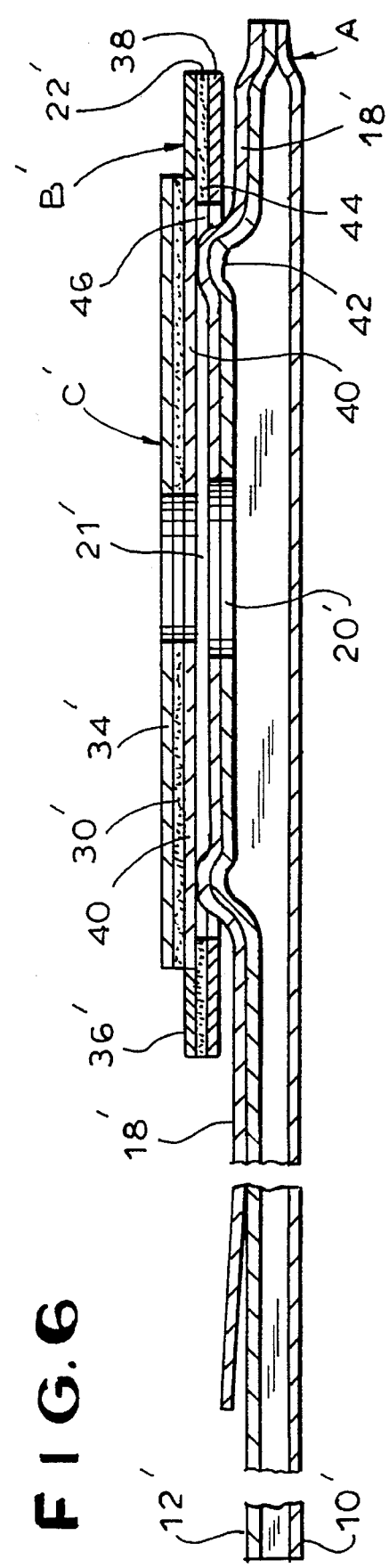

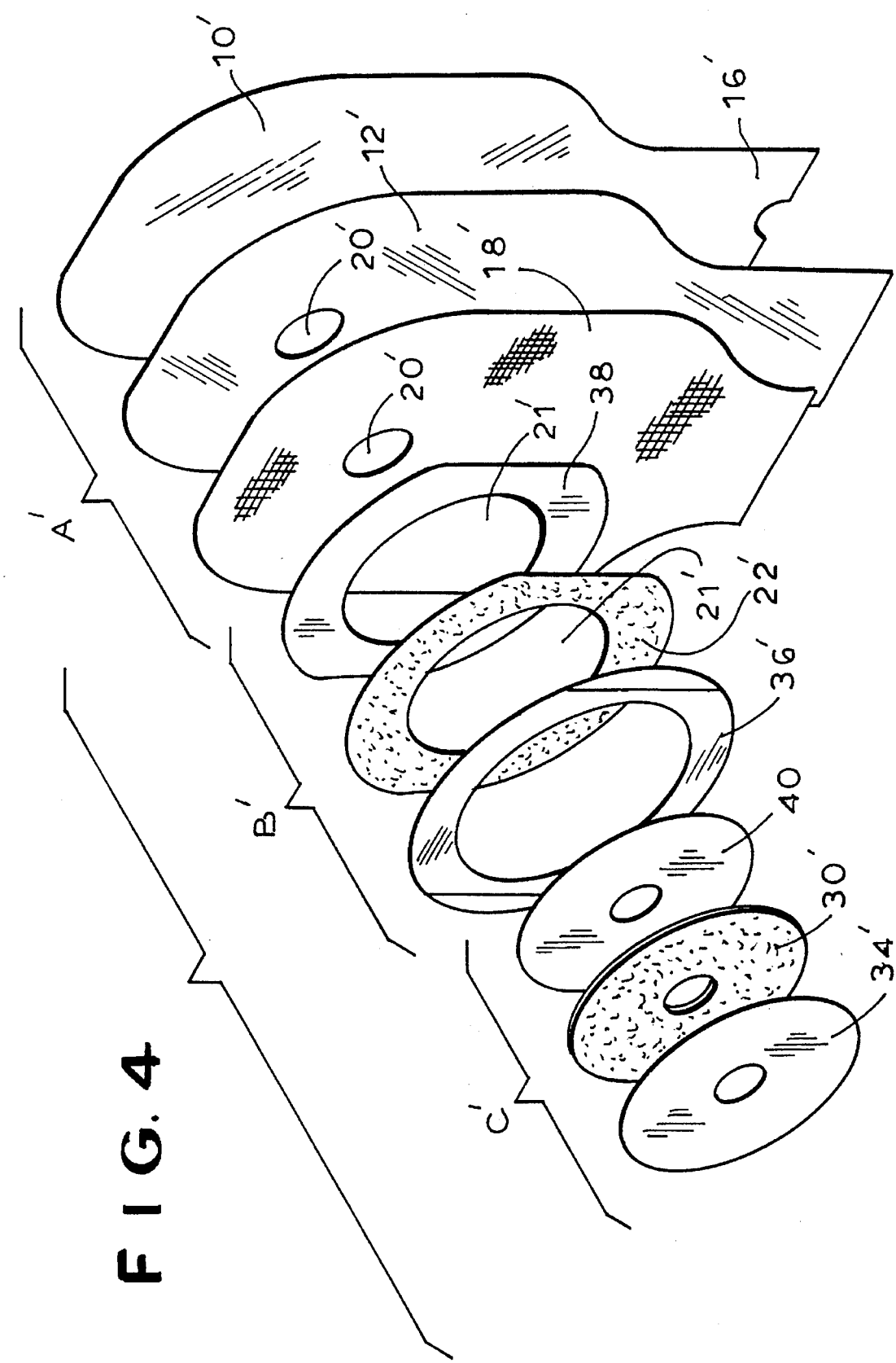

FIG. 8
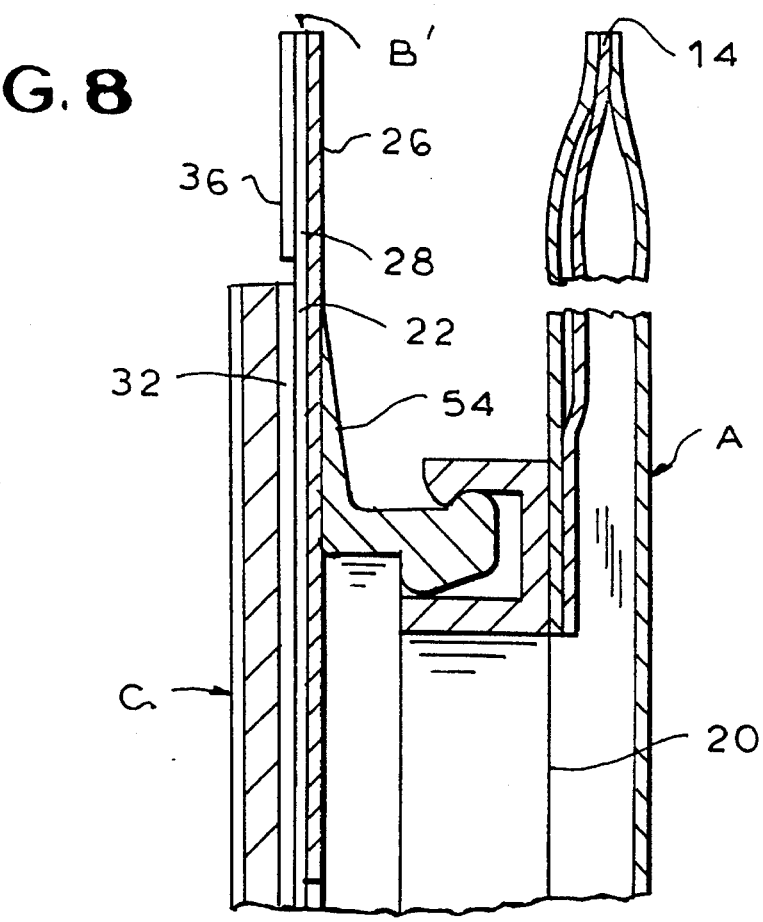
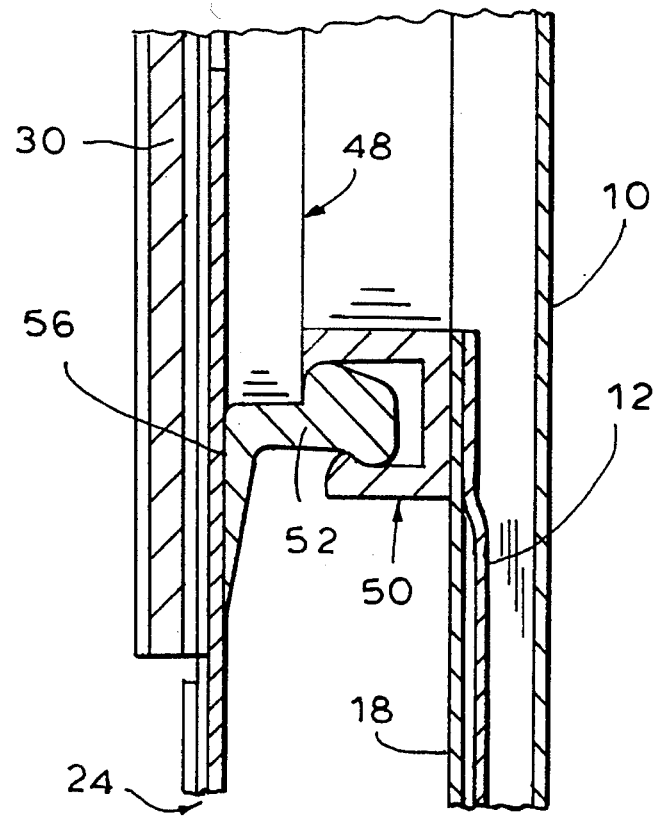

OSTOMY DEVICE

BACKGROUND OF THE INVENTION

The present invention relates to ostomy devices of the type including a waste collection pouch adapted to be adhesively affixed to the skin surrounding the stoma and more particularly to such a device which provides increased strength, improved breathability and better odor protection.

Certain surgical procedures known as colostomy, ileostomy and urostomy result in an opening in the abdominal wall, called a stoma, which permits waste discharge from the interior of a body cavity. Since the patient has no control over the waste discharge, it is often necessary for the patients who have undergone these surgical procedures to utilize an ostomy device to protect the stoma and collect the waste material as it is discharged.

Over the years, ostomy devices of a variety of different types and constructions have been utlized. Various materials and adhesives have been developed to increase the utility and wareability of same.

The basic device includes a collection receptacle or pouch connected to an adhesive coated faceplate which serves to mount the pouch to the body. The pouch includes first and second thin film walls which are sealed by heat welding or the like along the periphery. The pouch has an inlet opening designed to be aligned with the stoma and an outlet for emptying material from the pouch. In single piece devices, the pouch is permanently affixed to the adhesive coated faceplate. In two piece devices, the pouch is detachably mounted to the faceplate by coupling rings or the like, permitting the pouch to be replaced without removal of the faceplace each time.

For the ostomy device to function properly, it is important that it make a fluid-tight connection with the peristomal skin to prevent any liquid, solid, semi-solid or gaseous waste from escaping. It is also important to provide a weight bearing connection to support the weight of the device.

The proper functioning of the device also requires that the components of the device which are joined together during manufacture remain completely attached to each other over the entire period of use. One of the problems which is encountered is that it is difficult to reliably join the components together because of the different materials involved. Thus, during use of the device, components may begin to become detached. However, the materials are selected because of the specific properties required such as skin compatability, which is of primary importance.

This is particularly true of the hydrocolloid disk portion of the faceplate which forms a seal with the skin surrounding the stoma. The hydrocolloid material is commonly carried on a polyethylene film. This film acts as an odor barrier. It also provides a base for the disk to be secured to the pouch.

The disk carries an adhesive collar which is the other portion of the faceplate. The collar consists of a non-woven polyester material upon which the adhesive layer is situated. Although this polyester material is weldable, it cannot be welded to the pouch material because too high a temperature is required. Thus, the collar must be carried on the disk, which can be welded to the pouch.

The hydrocolloid disk and in particular the polyethylene film is welded to the pouch along a thin ring-like section which surrounds the relatively large pouch inlet opening. The collar has a central opening which must be large enough to accomodate the section of the disk which is welded to the pouch. The perpherial portion of the disk, outside of the welded section, is rather thin and is overlapped by the collar by a only small amount. The adhesive holds the collar on the disk only along this relatively thin overlapping area.

It has been found that in use, the hydrocolloid material may tend to separate from the polyethylene film. In addition, because of the large central opening required for collar, resulting in a relatively thin area for the adhesive bond with the disk film, the collar may tend to separate from the disk.

Another problem relates to odor. It has been found if fecal material in the pouch is absorbed into the hydrocolloid material, the hydrocolloid material in time will begin to give off an odor. The conventional polyethylene film does not completely protect against wicking of liquid stool material from inside the pouch.

These problems are overcome in the present invention through the use of different materials for the film of the hydrocolloid disk and for the collar, as well as a change in the shape of the collar. These material changes permit the collar to be welded directly to the pouch in the one piece appliance and be secured directly to the coupling ring in the two piece embodiment. The change in collar shape greatly increases the area in which the collar may be attached to the disk. This increases the overall strength of the device and reduces the possibility for the components becoming detached during use. These changes also result in improved skin breathability and serve to improve the effectiveness of the odor barrier.

SUMMARY OF THE INVENTION

It is, therefore, a prime object of the present invention to provide an improved ostomy device in which the hydrocolloid disk can adhere to the disk over a relatively large surface area.

It is another object of the present invention to provide an improved ostomy device in which the components of the hydrocolloid disk will not tend to separate during use.

It is another object of the present inventor to provide an improved ostomy device in which the collar may be secured directly to the pouch, in the one piece embodiment, and to the coupling ring, in the two piece embodiment.

It is another object of the present invention to provide an improved ostomy device with better odor protection.

It is another object of the present invention to provide an improved ostomy device which has greater breathability.

In accordance with one aspect of the invention, an improved ostomy device is provided comprising a pouch with an inlet. A faceplate is provided as are means for attaching the faceplate to the pouch. The faceplate includes a collar with a central opening which is aligned with the pouch inlet and a hydrocolloid member mounted to the collar. The collar includes a non-woven polyethylene member, a perforated EVA/polyethylene film and an adhesive layer.

In the one piece embodiment, the collar is welded directly to the pouch. The hydrocolloid member is attached to the collar over substantially the entire surface of the hydrocolloid member. In the two piece embodiment, the collar is secured directly to the coupling ring. The hydrocolloid member preferably includes a polyethylene/PVDC film.

The non-woven member of the collar has central opening smaller than the inlet. The adhesive layer covers substantially the entire surface of the non-woven member.

The perforated EVA/polyethylene film covers substantially the entire surface of the non-woven member. The adhesive is cast onto the EVA/polyethylene film. The EVA/polyethylene film is preferrably approximately 2 mils thick.

In accordance with another aspect of the present invention, an improved ostomy device is provided including a pouch with an inlet. A faceplate is provided as are means for attaching the pouch and the faceplate. The faceplate includes a collar with a central opening which is aligned with the inlet and a hydrocolloid member mounted to the collar. The hydrocolloid member includes a polyethylene/PVDC film.

The film is approximately 1 mil. thick and covers substantially the entire hydrocolloid member. In the one piece embodiment, the collar is welded directly to the pouch. The hydrocolloid member is attached to the collar over substantially the entire surface of the film. In the two piece embodiment, the collar is secured directly to the coupling ring.

The collar includes a non-woven polyethylene member, a perforated EVA/polyethylene film and an adhesive layer. The non-woven member has a central opening smaller than the inlet. The adhesive layer covers subtantially the entire surface of the non-woven member.

The perforated EVA/polyethylene film covers substantially the entire surface of the non-woven member. The adhesive is cast onto the EVA/polyethylene film. The EVA/polyethylene film is approximately 2 mils. thick.

In accordance with another aspect of the present invention, an improved ostomy device is provided, including a pouch with a wall having an inlet. An adhesive collar with a central opening is aligned with the pouch inlet. The collar is welded directly to the pouch wall. A hydrocolloid member is adhesively attached to the collar.

The collar includes a non-woven polyethylene member, a perforated EVA/polyethylene film and an adhesive layer. The hydrocolloid member includes a polyethylene/PVDC film. The hydrocolloid member is attached to the collar over substantially the entire surface of the polyethylene/PVDC film.

The non-woven member has a disk-like configuration with a central opening smaller than the inlet. The adhesive layer covers substantially the entire surface of the non-woven member.

The perforated EVA/polyethylene film also covers substantially the entire surface of the non-woven member. The adhesive is cast onto the EVA/polyethylene film.

In accordance with another aspect of the present invention, an improved ostomy device is provided including a pouch with a wall having an inlet. First and second coupling rings are provided. An adhesive collar with a central opening is secured to the coupling ring. A hydrocolloid member is attached to the collar. The second coupling ring is secured to the pouch.

The collar includes a non-woven polyethylene member, a perforated EVA/polyethylene film and an adhesive layer. The hydrocolloid member includes a polyethylene/PVDC film. The hydrocolloid member is attached to the collar over substantially the entire surface of the polyethylene/PVDC film.

The non-woven member has a central opening smaller than the inlet. The adhesive layer covers substantially the entire surface of the non-woven member.

The perforated EVA/polyethylene film also covers substantially the entire surface of the non-woven member. The adhesive is cast onto the EVA/polyethylene film.

To these and such other objects which may hereinafter appear, the present invention relates to an improved ostomy device as set forth in detail in the following specification and recited in the annexed claims, taken together with the accompanying drawings, wherein like numerals refer to like parts and in which.

BRIEF DESCRIPTION OF THE DRAWINGS

FIG. 3 is a section view of the device of FIG. 1;

FIG. 4 is an exploded isometric view of a commercially available device;

FIG. 6 is a plan view of the device of FIG. 4;

FIG. 8 is a cross sectional view of the second preferred embodiment.

DETAILED DESCRIPTION OF THE INVENTION

Figure 1:
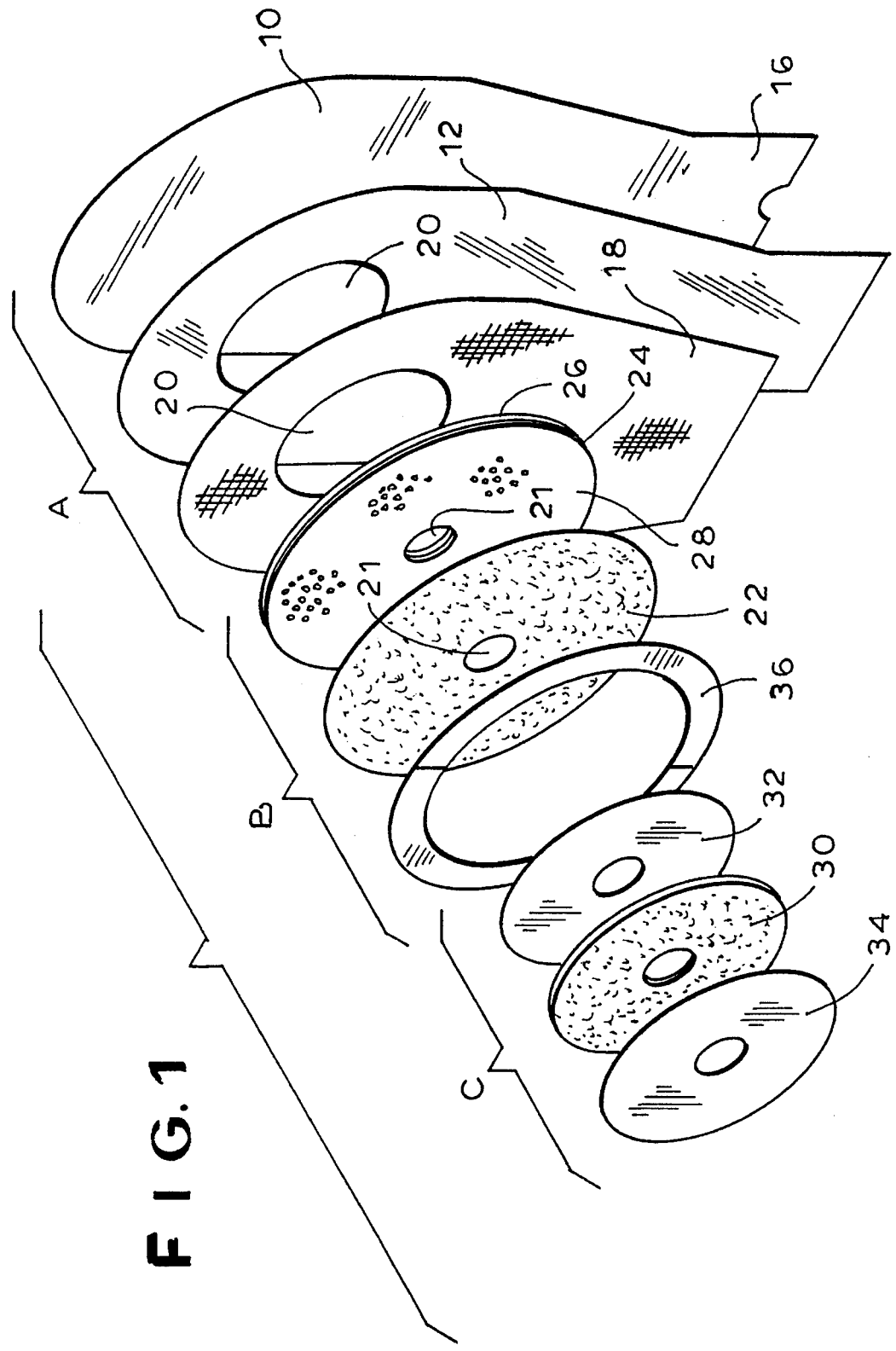
FIG. 1 is an exploded isometric of a first preferred embodiment the ostomy device of the invention.
Figure 2:
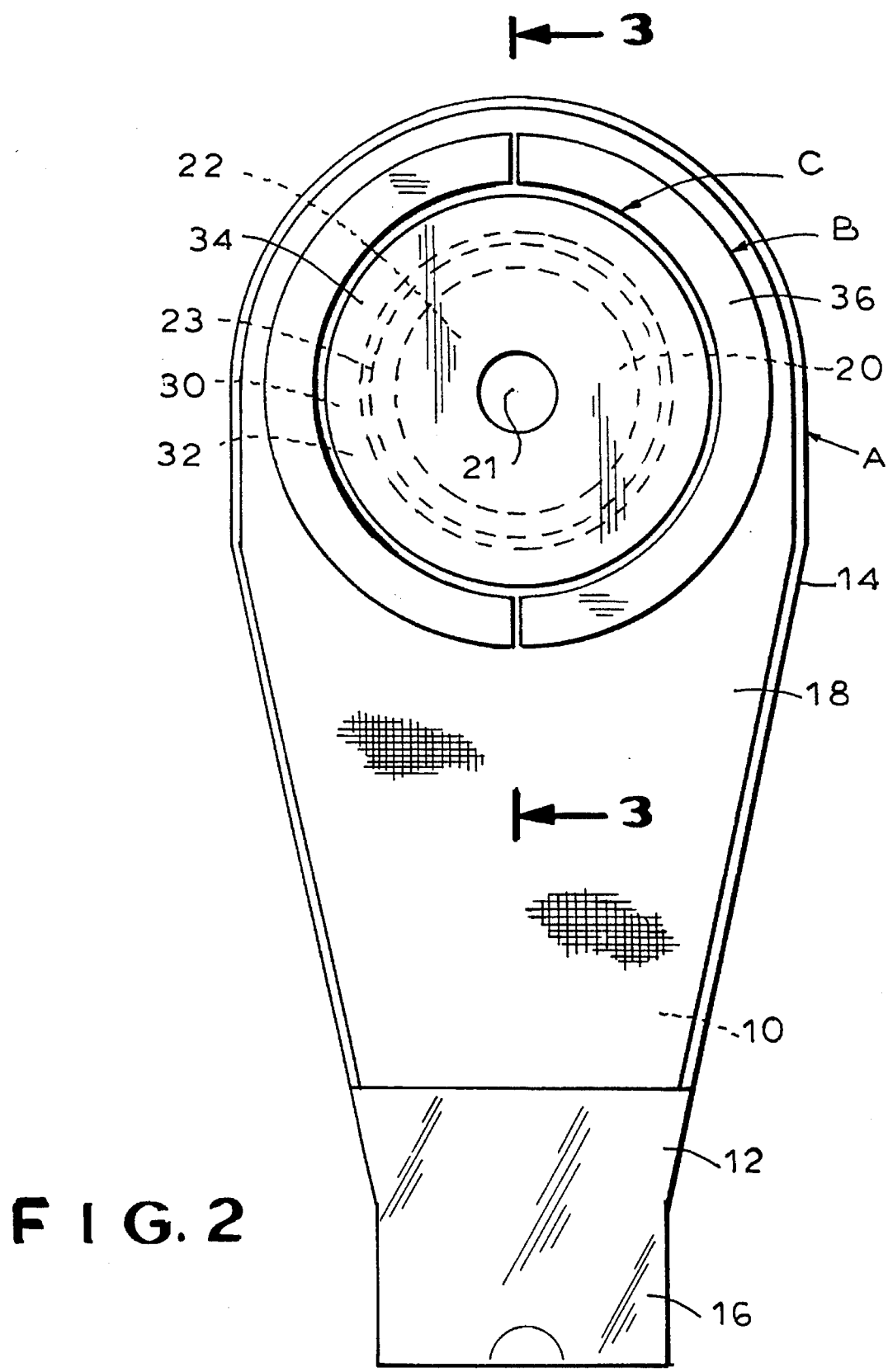
FIG. 2 is a plan view of the device of FIG. 1.

The first preferred embodiment of the present invention is the single piece device illustrated in FIGS. 1, 2 and 3. It includes a collection pouch, generally designated A. A microporous adhesive collar, provided for securing the pouch to the skin of the user, is generally designated B. A hydrocolloid disk, generally designated C, serves to seal the device to the skin surrounding the stoma.

Pouch A has a front wall 10 and a rear wall 12 made of thin, flexible film which is heat welded around the periphery 14 to form an enclosed receptacle. Depending upon the type of stomal discard, the pouch may include drainable outlet 16 which is sealed with a clip or it may include a liquid drainable top valve or the bottom merely be sealed in the same manner as periphery 14.

The films from which the pouch may be made are selected from materials which possess the properties of being moisture impermeable, odor impermeable and capable of being heat sealed or impulse welded. Suitable materials include polyethylene, co-polymers of polyethylene and ethylene vinyl acetate, co-polymers of vinyl chloride and polyvinylidene chloride and laminates thereof. The pouch walls are preferably from about two to four mils thick.

In some cases, it is desirable, in order to enhance the comfort of the patient, to use a flocking material 18 for lining the exterior surface of pouch wall 12. Flocking material 18 preferably has its smooth side outwards.

An inlet opening 20 is provided in rear pouch wall 12 and flocking sheet 18. Microporous collar B is welded directly to the exposed surface of flocking sheet 18. Collar B is disk-like in configuration and has a central opening 21 which is smaller in diameter than inlet opening 20 in pouch A, but is aligned therewith.

Collar B consists of a pressure sensitive adhesive layer 22 cast onto a backing 24. Layer 22 is preferrably 4 mils thick. The adhesive layer can be an acrylic microporous adhesive as taught by Copeland in U.S. Pat. No. 3,121,021, a microporous hydrocolloid adhesive as taught by Cilento in U.S. Pat. No. 4,427,727, or a polyisobutylene—hydrocolloid containing adhesive as taught by Chen in U.S. Pat. No. 3,339,546, by Chen et al. in U.S. Pat. No. 4,192,785, by Pawelchak in U.S. Pat. No. 4,393,080, or it can be adhesive composition containing a styrene type block copolymer in addition to the polyisobutylene and hydrocolloids as taught by Doyle et al. in U.S. Pat. No. 4,551,490.

The backing 24 of the invention includes a non-woven polyethlyene material 26. An EVA/polyethylene perforated film 28, approximately 2 mils thick, is bonded to one surface of non-woven 26. Adhesive 22 is cast over film 28. The other surface of non-woven material 26 is welded to pouch A along section 23 (FIG. 2).

Disk C consists of an adhesive layer 30 situated on a film 32. Adhesive layer 30 can be any pressure sensitive adhesive suitable for use on human skin. Preferably, the adhesive consists of a elastomeric substance such as polyisobutylene containing one or more hydrocolloids as taught by Chen in U.S. Pat. No. 3,339,546, by Chen et al. in U.S. Pat. No. 4,192,785, by Pawelchak in U.S. Pat. No. 4,393,080 or it can additionally include a styrene type block co-polymer as taught by Doyle et al. in U.S. Pat. No. 4,551,490. Adhesive layer 30 is preferably from about 20 to 70 mils thick.

Film 32 is composed of polyethylene and PVDC (polyvinlydene copolymer) approximately 0.5 to 1 mil thick. It covers the entire surface of disk C. The surface of film 32 adheres to collar adhesive 22 to attach disk C to collar B over substantially the entire surface area of the disk.

Situated over the surface of adhesive layer 30 and the exposed portion of adhesive layer 22 is a disk 34 and ring 36 respectively of 5 mil silicone release paper. This paper is used to protect the adhesive surfaces until use.

Figure 5:
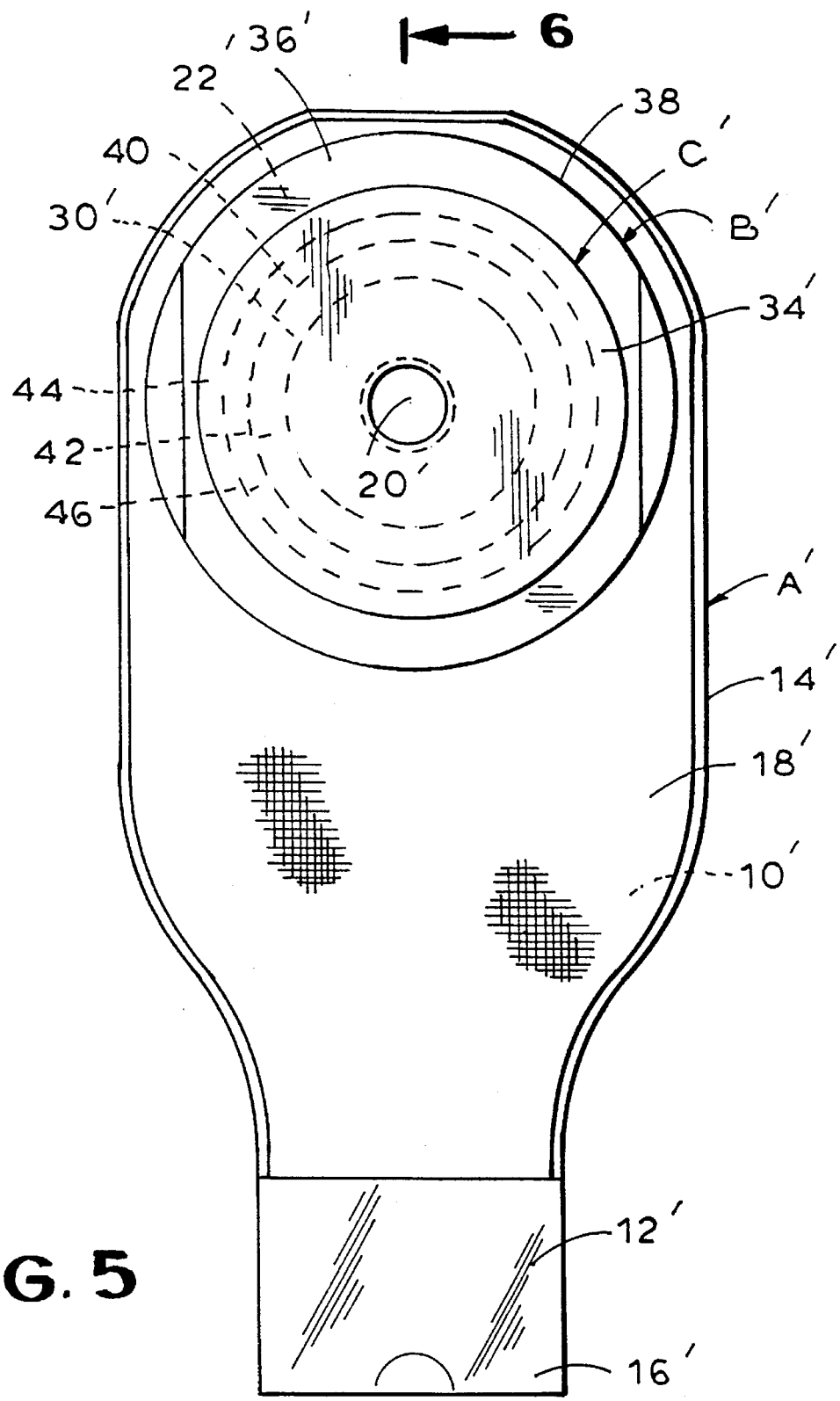
FIG. 5 is a sectional view of the device of FIG. 4.

FIGS. 4, 5 and 6 illustrate a commercially available device currently marketed by the assignee hereof. In this device, the pouch A' is similar to pouch A, including walls 10' and 12' as well as flocking 18'. However, inlet 20' is smaller than inlet 20. Collar B' consists of a layer of acrylic adhesive 22' similar to layer 22 but it is situated on a non-woven ring 38 made of polyester.

The central openings 21' in layer 22' and in non-woven 38 must be much larger than the central openings 21 in the corresponding components 22 and 24 of collar B because, in this device, it is disk C' which is welded to the pouch, not the collar. Disk C' includes an adhesive layer 30' on a backing of film 40 composed of polyethylene. Adhesive 30' is of the same composition as layer 30 and is covered by release paper 34'. A ring of release paper 36' covers the exposed surface of adhesive 22'.

As best seen in FIG. 6, disk C' is welded to pouch A' along ring-like section 42. Collar B' is affixed to disk C', and more particularly to the perpherial portion of the surface of film 40, along a concentric ring-like section 44 which is spaced a small distance 46 from section 42. Section 42, which is the only place where collar B' is attached to disk C', is relatively thin A comparison of the device of the invention shown in FIGS. 1, 2 and 3 and the commercially available device of FIGS. 4, 5 and 6 shows several significant material and structural differences. First, in the invention, because of the composition of the collar (non-woven polyethylene material coated with a EVA/polyethylene film), the collar can be welded directly to the pouch wall. Since the disk need not be welded to the pouch, the collar may be formed with a central opening which is much smaller. The smaller central opening permits the entire surface of the hydrocolloid disk, specifically that of the polyethylene/PVDC film, to adhere to the collar. A great improvement in the strength of the overall device is achieved in this way and the possibility separation of joined components during use is greatly reduced.

Second, the use of a polyethylene/PVDC film 32 in the invention as a backing layer for disk C serves to increase the protection of the hydrocolloid from fecal material leading to a more effective odor barrier. Since film 32 covers the entire hydrocolloid layer, wicking of liquid stool material from the pouch is reduced.

The use of a perforated film 28 on the non-woven 26 provides an excellent base for adhesive 22. At the same time, it retains the breathability feature necessary for the collar to be skin friendly.

The film 28 is preferrably perforated using 0.03 diameter holes in a pattern, typically 0.125 staggered. The non-woven 26 is LDPE micro spin bonded, 30 g–35 g weight.

Figure 7:
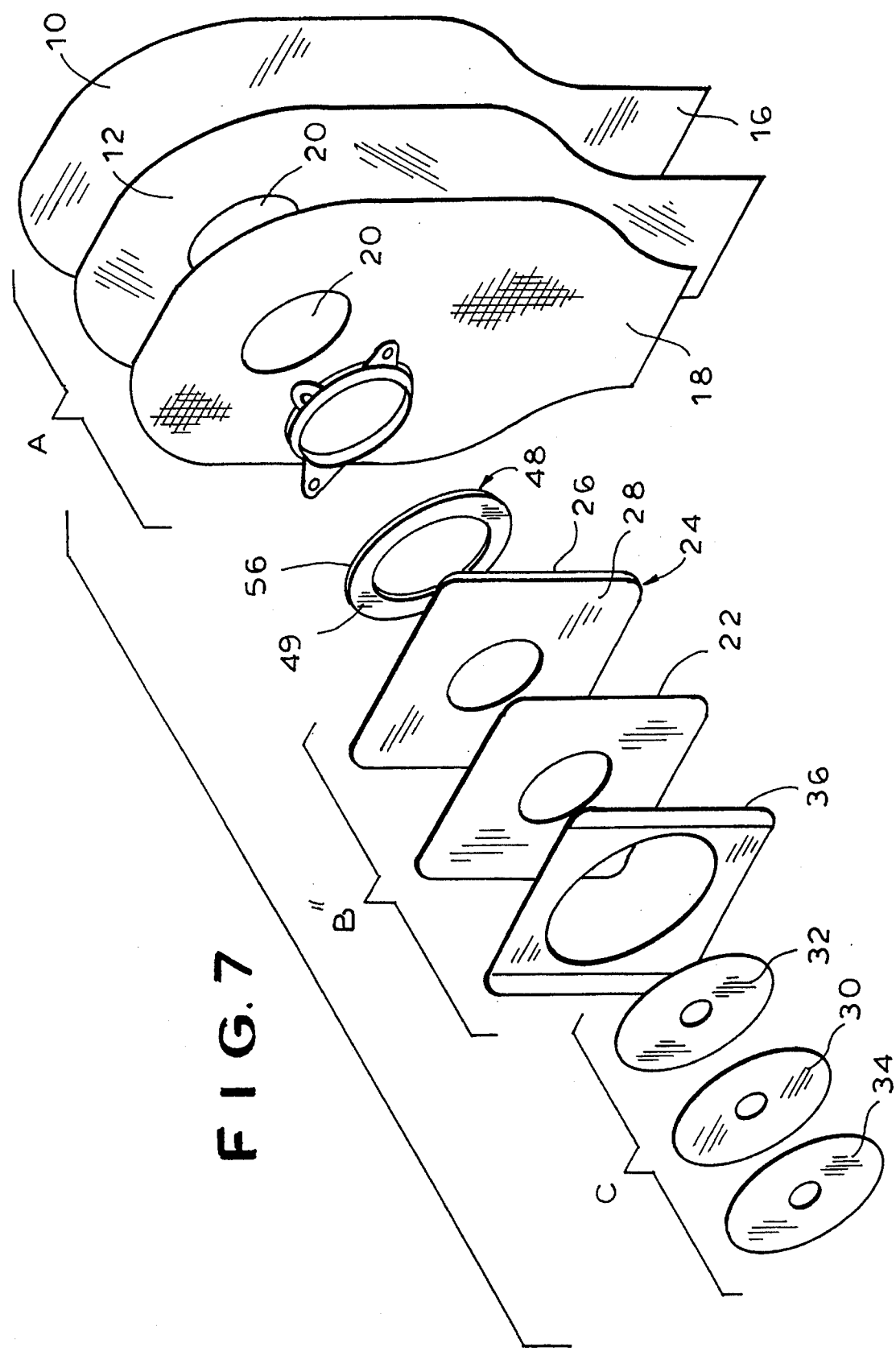
FIG. 7 is an exploded isometric of a second preferred embodiment of the present invention.

FIGS. 7 and 8 show a second preferred embodiment of the present invention, which is a two piece device. This embodiment differs from the first preferred embodiment only with respect to the use of detachable coupling members interposed between the collar and the pouch.

In the two piece embodiment, like the single piece embodiment, pouch A consists of walls 10 and 12, flocking 18 and inlet opening 20. Disk C consists of polyethylene/PVDC film 32 and an adhesive layer 30 covered by protective release paper 34. Collar B" has a rectangular configuration. Like collar B of FIGS. 1, 2 and 3, it consists of an adhesive layer 22 cast onto a backing 24 made of non-woven material 26 and an EVA/polyethylene perforated film 28. Adhesive layer 22 is covered by release paper 36. Disk C adheres to adhesive layer 22 of collar B".

The difference in this embodiment relates to coupling rings 48 and 50. Ring 48 is attached to the faceplate and consists of an annular protrusion 52 axially extending from a radially extending base 54. As best seen in FIG. 8, collar B" and more particularly now woven material 26, is secured directly to surface 58 of base 54 by welding or adhesive.

Ring 50 consists of an annular channel and is secured to pouch A in alignment with inlet opening 20. The engagement of rings 48 and 50 releaseably secures the faceplate consisting of collar B" and disk C to pouch A.

This embodiment has all of the advantages of the first embodiment, including greater strength, increase odor protection and improved breathability. It has the additional advantage that the pouch is detachable from the faceplate to permit the pouch to be changed without the necessity of removal of the faceplate.

It will now be appreciated that the present invention relates to an ostomy device with increased strength, improved skin breathability and better odor protection. These advantages are achieved through the use of a EVA/polyethylene perforated film/non-woven polyethylene collar, which is welded directly to the pouch in the one piece embodiment and secured to the coupling ring in the two piece embodiment. The hydrocolloid disk includes an adhesive with a polyethylene/PVDC film backing. The disk adheres over a large portion of its surface to the acylic adhesive of the collar.

While only a limited number of preferred embodiments have disclosed for purposes of illustration, it is obvious that many modifications and variations could be made thereto. It is intended to cover all of these modifications and variations which fall within the scope of the invention, as recited by the following claims.

I claim:

1. An ostomy device comprising:

a pouch with an inlet in a sidewall;

a faceplate proximate to said inlet attachable to said sidewall, said faceplate including a collar with a central opening adapted to align with said pouch inlet, said collar including a perforated EVA/polyethylene film between a non-woven polyethylene layer and an adhesive layer, and a hydrocolloid member having substantially an entire surface secured to said adhesive layer so as to securely join said hydrocolloid member to said collar; and attaching means for attaching said faceplate to said pouch by welding said collar to said pouch.

2. The device of claim 1 wherein said hydrocolloid member includes a polyethylene/PVDC film.

3. The device of claim 2 wherein said polyethylene/PVDC film covers substantially the entire surface of said hydrocolloid member.

4. The device of claim 1 wherein said non-woven layer has a central opening smaller than said pouch inlet.

5. The device of claim 1 wherein said perforated EVA/polyethylene film covers substantially an entire surface of said non-woven layer.

6. The device of claim 1 wherein said adhesive layer is cast onto said EVA/polyethylene film.

7. The device of claim 1 wherein said EVA/polyethylene film is approximately 2 mils thick.

8. The device of claim 1 wherein said attaching means includes first and second coupling rings and wherein said collar is secured to said first coupling ring and said second coupling ring is secured to said pouch.

9. An ostomy device for receiving body waste comprising:

a pouch with an inlet in a sidewall for receiving the waste; and a faceplate proximate to said inlet attachable to said sidewall, said faceplate including a collar with a central opening adapted to align said opening with said inlet and to attach to said pouch, and a hydrocolloid member having a backing of a polyethylene/PVDC film secured to said collar, said film protecting the hydrocolloid member from soiling by the body waste received in said pouch.

10. The device of claim 9 wherein said film is approximately 1 mil. thick.

11. The device of claim 9 wherein said polyethylene/PVDC film covers substantially the entire surface of said hydrocolloid member.

12. The device of claim 9 further comprising means for securing said collar to said pouch.

13. The device of claim 9 wherein said hydrocolloid member is attached to said collar over substantially an entire surface of said film.

14. The device of claim 12 wherein said means for securing includes first and second coupling rings and wherein said collar is secured to said first coupling ring and said second coupling ring is secured to said pouch.

15. The device of claim 9 wherein said collar includes a non-woven polyethylene member, a perforated EVA/polyethylene film and an adhesive layer.

16. The device of claim 15 wherein said non-woven member has a central opening smaller than said pouch inlet.

17. The device of claim 15 wherein said perforated EVA/polyethylene film covers substantially an entire surface of said non-woven member.

18. The device of claim 15 wherein said adhesive layer is cast onto said EVA/polethylene film.

19. The device of claim 15 wherein said EVA/polyethylene film is approximately 2 mils. thick.

20. An ostomy device comprising:

a pouch with an inlet in a sidewall for receiving waste;

an adhesive non-woven collar having a central opening aligned with said pouch inlet;

securing means for securing said collar directly to said sidewall of said pouch; and a hydrocolloid member secured to said collar over substantially the entire surface of said hydrocolloid member, wherein said collar comprises a perforated EVA/polyethylene film between a non-woven polyethylene member and an adhesive layer.

21. The device of claim 20 wherein said hydrocolloid member comprises a polyethylene/PVDC film.

22. The device of claim 21 wherein said polyethylene/PVDC film covers substantially an entire surface of said hydrocolloid member.

23. The device of claim 20 wherein said non-woven member has a central opening smaller than said pouch inlet.

24. The device of claim 20 wherein said perforated EVA/polyethylene film covers substantially an entire surface of said non-woven member.

25. The device of claim 20 wherein said adhesive layer is cast onto said EVA/polyethylene film.

* * * * *